United States Patent [19]

Kajiwara

[11] Patent Number: 5,119,789
[45] Date of Patent: Jun. 9, 1992

[54] FUEL SUPPLY REGULATING APPARATUS
[75] Inventor: Yasuya Kajiwara, Himeji, Japan
[73] Assignee: Mitsubishi Denki Kabushiki Kaisha, Tokyo, Japan
[21] Appl. No.: 728,507
[22] Filed: Jul. 11, 1991
[30] Foreign Application Priority Data
Jul. 13, 1990 [JP] Japan .................................. 2-184150
[51] Int. Cl.$^5$ ...................... F02D 19/08; G01N 21/17
[52] U.S. Cl. .................................. 123/494; 123/1 A; 73/116
[58] Field of Search .......................... 123/14, 494, 575; 73/61.1 R, 116; 250/343, 345; 356/135, 136

[56] References Cited

U.S. PATENT DOCUMENTS

| 4,438,749 | 3/1984 | Schwippert ........................ 123/494 |
| 4,594,968 | 6/1986 | Degobert et al. ............... 123/494 X |
| 4,962,746 | 10/1990 | Miyata et al. .................. 123/1 A X |
| 5,044,344 | 9/1991 | Tuckey et al. .................. 123/494 X |

Primary Examiner—Tony M. Argenbright
Attorney, Agent, or Firm—Sughrue, Mion, Zinn, Macpeak and Seas

[57] ABSTRACT

An apparatus for regulating fuel supply according to fuel mixture ratio comprising a light source (5) for radiating a light beam (7) through fuel (3), a light path defining unit (26) for defining a light path for the light beam (7) in accordance with a refraction ratio of the fuel, and a light receiver (24) for receiving the light beam passed through the fuel. The light receiver (24) has connected thereto an actuator (32,43,47) for moving at least one of the light source (5), the light path defining unit (26) and the light receiver (24) by an amount sufficient to keep the light beam (7) always impinging at a constant position on the light receiver (24). The actuator (47) is connectable to a fuel regulator (46,48) for adjusting the fuel supply to an engine in accordance with the amount of the movement of the above components.

7 Claims, 3 Drawing Sheets

FUEL SUPPLY REGULATING APPARATUS

BACKGROUND OF THE INVENTION

This invention relates to a fuel supply regulating apparatus and, more particularly, to a fuel supply regulating apparatus for regulating the fuel supply to an engine in accordance with the fuel mixture ratio of the fuel such as the methanol concentration in gasoline.

FIG. 5 illustrates, in a schematic diagram, the main portion of a conventional fuel property detecting apparatus disclosed in Japanese Patent Laid-Open No. 58-129235, for example. In FIG. 5, a transparent prism 1 of a triangular cross-section has jointed thereon a similar but hollow triangular prism 2 through which fuel 3 flows. These transparent prisms 1 and 2 are held together by a housing 4 which has on its opposite sides openings 4a.

Adjacent to the housing 4, a light source 5 is disposed to face to one of the openings 4a of the housing 4 through a slit plate 6 which shapes the light from the light source 5 into a light beam 7.

On a light path of an outcoming light beam 7a from the second opening 4a, a light amount detection plate 8 is provided. The light amount detection plate 8 has formed therein a longitudinal slit 9 having a gradually changing width. A collective lens 10 is disposed for collecting and focusing the light beam passing through the slit 9 onto a light sensor 11 which senses the amount of light that impinges on the light sensor 11. The light sensor 11 has connected thereto a controller 12 for controlling the fuel supply to an engine (not shown), such as by controlling the period of time during which the fuel injection valve (not shown) is opened or the degree of opening of the fuel pressure regulator (not shown).

The operation will now be described. The light beam 7 emitted from the light source 5 passes through the slit plate 6 and into the hollow transparent prism 2, from where the light beam 7 travels from the fuel 3, the hollow prism 2 and through the solid prism 1 while being refracted at each interface, and is emitted from the housing 4 through the second opening 4a to impinge upon the light amount detection plate 8.

The light 7a reached to the light amount detection plate 8 only partially passes through the slit 9 because of the limited width of the slit 9, and is collected by the collecting lens 10 to be focused on the light amount sensor 11.

The refraction factor at an interface A between the fuel 3 and the hollow transparent body 2 varies in accordance with the characteristics of the fuel, i.e., the ratio of mixture of the different kinds of fuels within the fuel 3. Therefore, when the mixture ratio changes, the refraction angle at the interface A varies and the position at which the light beam 7a impinges at the light amount detection plate 8 varies accordingly in the longitudinal direction (up and down directions in the figure). On the other hand, since the slit 9 of the light amount detection plate 8 is longitudinally tapered, the light amount detected by the light amount sensor 11 varies in accordance with the ratio of mixture of the different fuels in the fuel 3.

As the light amount sensor 11 detects the light, a signal according to the light amount is provided to the control unit 12, and thus the control unit 12 controls the valve opening time of the fuel injection valve and the fuel pressure regulator in accordance with the signal.

The above operation will now be described in more detail using an example in which a different fuel of methanol is mixed into gasoline.

When the fuel 3 contains only gasoline which has a refraction factor of about 1.51 which is relatively small, the position at which the light beam 7a impinges at the light amount detection plate 8 is on the upper portion of the plate as viewed in the figure, so that the light amount that can pass through the slit 9 is decreased.

On the other hand, when methanol which has a refraction factor of about 1.33 is mixed with gasoline which has a refraction factor of about 1.51, the resultant refraction factor of the mixed fuel is a value between 1.33 and 1.51 which varies according to the mixed ratio. That is, as the ratio of amount of methanol within the fuel increases, the refraction factor of the fuel 3 decreases, so that the refraction angle becomes small and the position at which the light beam 7a impinges upon the light amount detection plate 8 moves to a lower position as viewed in the figure. Thus, the light amount that passes through the slit 9 increases as the mixture ratio of methanol increases.

Thus, since the light amount that is received by the light amount sensor 11 varies in accordance with the mixture ratio of methanol in gasoline, the fuel character can be determined by measuring the light amount.

Other types of the conventional design is also known in which the position at which the light beam 7a impinges can be directly detected by a semiconductor element, a diode array, an image sensor or the like to determine the fuel characteristics.

In the conventional fuel supply regulating apparatus as above described, the refraction factor of the fuel 3 is measured by the signal from the light amount sensor 11, and a separate control unit 12 for controlling a fuel pressure regulator, a fuel injection valve actuator or the like on the basis of the above measured results is necessary, so that the system is disadvantageously expensive.

SUMMARY OF THE INVENTION

Accordingly, an object of the present invention is to provide a fuel supply regulating apparatus free from the above discussed problems.

Another object of the present invention is to provide a fuel supply regulating apparatus which is simple in structure.

A further object of the present invention is to provide a fuel supply regulating apparatus which makes the fuel supply system simple and less expensive.

With the above objects in view, according to the present invention, the apparatus for regulating fuel supply according to fuel mixture ratio comprises a light source for radiating a light beam through a fuel, and light path defining means for defining a light path for the light beam in accordance with a refraction ratio of the fuel, and light receiving means for receiving the light beam passed through the fuel. The apparatus also comprises actuator means connected to the light receiving means for moving at least one of the light source, the light path defining means and the light receiving means by an amount sufficient to keep the light beam impinging at a constant position on the light receiving means. The actuator means is also connected to fuel regulator means for adjusting the fuel supply to an engine in accordance with the amount of movement of the above-named components.

BRIEF DESCRIPTION OF THE DRAWINGS

The present invention will become more readily apparent from the following detailed description of the preferred embodiments of the present invention taken in conjunction with the accompanying drawings, in which.

DESCRIPTION OF THE PREFERRED EMBODIMENTS

Figure 1:
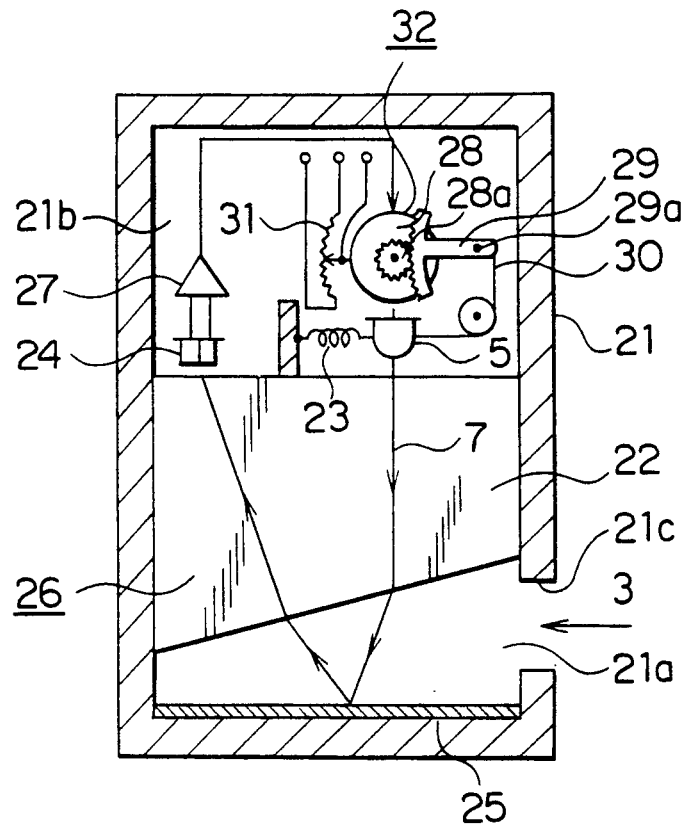
FIG. 1 is a schematic diagram illustrating one embodiment of the fuel supply regulating apparatus of the present invention.
Figure 5:
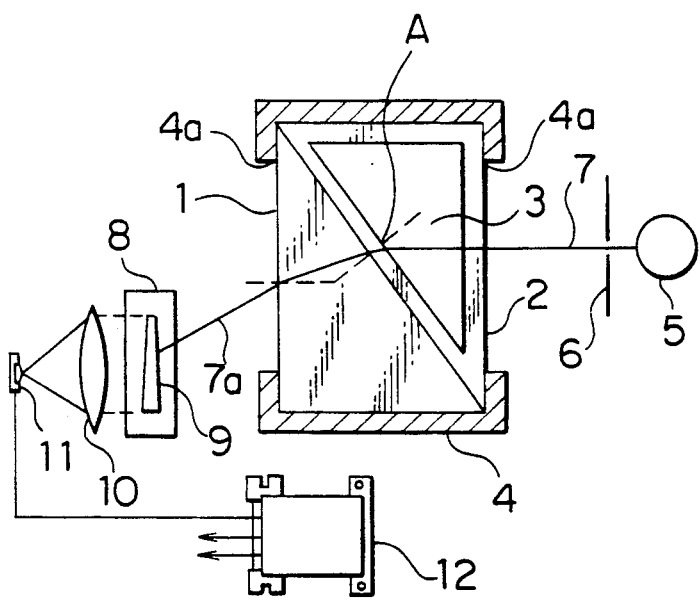
FIG. 5 is a schematic diagram illustrating one example of the conventional fuel supply regulating apparatus.

FIG. 1 is a schematic diagram illustrating the fuel supply regulating apparatus of the present invention, in which the components identical to or corresponding to those shown in FIG. 5 are designated by the same reference numeral, so that their explanation will not be repeated.

In the figure, a prism 22 having a substantially trapezoidal cross section is held within a housing 21, and a fuel chamber 21a and a space 21b are provided on the opposite sides of the prism 22. Fuel 3 flows into the fuel chamber 21a through an opening 21c.

Within the space 21b, a light source 5 for emitting a light beam 7 through the fuel 3 is disposed in opposition to the prism 22. The light source 5 is transversely slidable as viewed in the figure and is biased by a tension spring 23 toward left in the figure. Also within the space 21b, a light receiving unit 24 is provided in opposition to the prism 22 and paced apart from the light source 5 for receiving the light beam 7 passed through the fuel 3. The light receiving unit 24 comprises a photodiode divided into two halves or a dual light sensor.

On a surface of the fuel chamber 21a facing the prism 22, a reflector mirror 25 is positioned for reflecting the light beam 7 from the light source 5. The reflecting mirror 25 and the prism 22 constitute a light path defining unit 26 for defining a light path for the light beam 7 in accordance with a refraction ratio of the fuel 3.

The light receiving unit 24 has connected thereto a motor 28 through a differential amplifier 27. The motor 28 has on its rotary shaft a pinion 28a which is in mesh with one end of a sector gear 29 which is rotatably supported by the shaft 29a. The other end of the gear 29 is connected to the movable light source 5 through rope 30. The rotary shaft of the motor 28 has connected thereto a potentiometer 31 having a slider movable in response to the rotation of the motor 28. Although not illustrated, output of the potentiometer 31 is connected to a regulator such as a fuel pressure regulator or an actuator of a fuel injection valve or the like.

The fuel supply regulating apparatus also comprises an actuator unit 47 connected to the light receiving unit 24 for moving the slidable light source 5 by an amount sufficient to maintain the light beam 7 impinging at a fixed position on the light receiving unit 24. The actuator unit 47 comprises the differential amplifier 27, the motor 28, the gear 29, the rope 30 and the potentiometer 31. The actuator unit 47 is also connected to the fuel regulator such as the fuel pressure regulator or the actuator of the fuel injection valve or the like for adjusting the fuel supply to an engine in accordance with the displacement of the movable light source 5.

The collimated light beam 7 emitted from the light source 5 perpendicularly impinges upon and enters into the transparent prism 22. The light beam 7 travels through the prism 22 and enters into the fuel 3, whereupon the light beam 7 is refracted at the interface between the fuel 3 and the prism 22 according to the refraction factor of the fuel 3. Then, the light beam 7 is reflected at the reflector mirror 25 back to the fuel 3 and is refracted again at the interface between the fuel 3 and the prism 22 to travel through the prism 22 and impinges upon the light receiving unit 24.

The light receiving unit 24, when the light beam 7 is received, the respective photo diodes allows currents in accordance with their amount of received light to flow to the differential amplifier 27. In the differential amplifier 27, the difference between the currents from the respective photo diodes is generated and amplified to be supplied to the motor 28 as an output motor control signal.

The drive force of the motor 28 is transmitted to the slidable light source 5 through the pinion 28a, the gear 29 and the rope 30 to move the light source 5 to the transverse direction as viewed in the figure. At the same time, the slider of the potentiometer 31 displaces in response to the amount of rotation of the motor 28 whereupon the actuator of the fuel pressure regulator or the fuel injection valve or the like is automatically operated.

When the light beam 7 impinges upon the center of the light receiving unit 24, the light amounts received at the respective photodiodes balance each other and the displacement of the light source 5 does not take place.

If the refraction factor of the fuel 3 is lowered, for example, the refraction factor at the interface between the prism 22 and the fuel 3 increases, so that the position at which the light beam 7 impinges upon the light receiving unit 24 shifts leftward in the figure. Then, the photo diode of the leftside receives more light than the rightside diode. Therefore, the light source 5 is shifted to the right in the figure and the light beam 7 is also shifted to the right to reduce the difference between the light amounts on the two photo diodes of the light receiving unit 24 until the difference in the light amount received at the photo diodes becomes zero, upon which the motor 28 stops.

As has been described, according to the above-described embodiment of the fuel supply regulating apparatus of the present invention, the amount of rotation of the motor 28 corresponds to the amount of change in the refraction factor of the fuel 3 or the amount of change in the ratio of mixture of the different fuels, and the rotation of the motor 28 causes the actuator of the fuel pressure regulator, the fuel injection valves or the like to be operated according to the rotation thereof. Therefore, the control unit 12 which was necessary in the conventional apparatus is not needed and can be removed, so that the overall system of the fuel supply apparatus of an internal combustion engine can be made simple and inexpensive.

Figure 2:
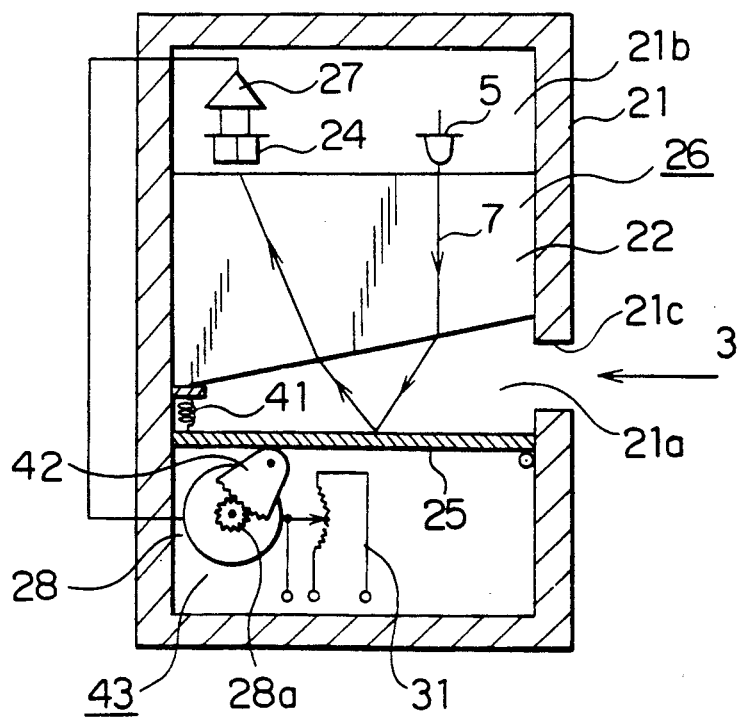
FIG. 2 is a schematic diagram illustrating another embodiment of the fuel supply regulating apparatus of the present invention.

FIG. 2 illustrates another embodiment of the fuel supply regulating apparatus of the present invention, in which the light source 5 and the light receiving unit 24 are fixed, and the reflecting mirror 25 which is a part of the light path defining unit 26 is rotatable about its right-hand end as viewed in the figure. The other end of the reflecting mirror 25 is biased downward by the compression spring 41 and is vertically movable by the gear 42 connected to the motor 28.

A fuel chamber 21a is defined between the reflecting mirror 25 and the prism 22, and the motor 28, the potentiometer 31 and the gear 42 are disposed within the space defined below the reflecting mirror 25. Also, the actuator unit 43 of this embodiment is composed of the differential amplifier 27, the motor 28, the gear 42 and the potentiometer 31. In other respects, the structure is the same as that described and illustrated in conjunction with FIG. 1.

In the fuel supply regulating apparatus of this embodiment, when the refraction factor of the fuel 3 is changed and the impinging position of the light beam 7 on the light receiving unit 24 shifts, a signal responsive to the change of the refraction factor is supplied from the differential amplifier 24 in a similar manner to the previous embodiment. This causes the motor 28 and the gear 42 to rotate to change the angle of the reflecting mirror 25 thereby to shift the light path of the light beam 7 until the light beam 7 impinges at the center of the light receiving unit 24, whereupon the further rotation of the motor 28 is stopped. This rotation of the motor 28 causes the potentiometer 31 to be operated, so that the actuators of the fuel pressure regulator and the fuel injection valves and the like are actuated accordingly.

In this embodiment also, the motor 28 rotates in accordance with the change of the refraction factor of the fuel 3, and the actuators for controlling the fuel supply to the internal combustion engine (not shown) are operated by the actuator unit 43, so that advantageous results similar to those obtain in the previous embodiment illustrated in FIG. 1 are obtained.

Figure 3:
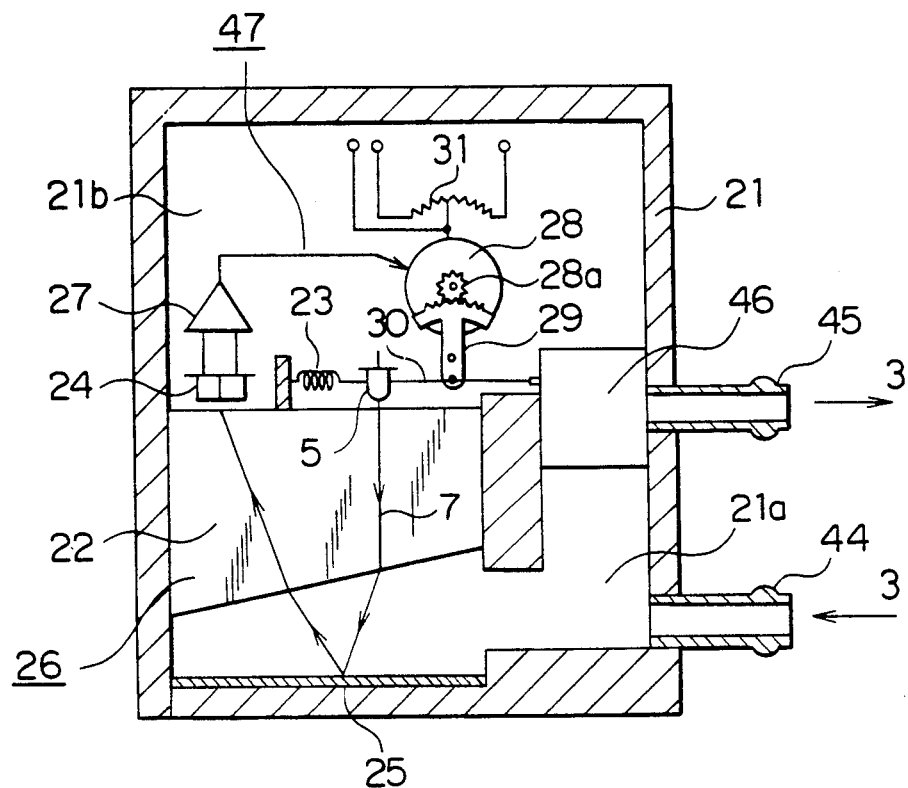
FIG. 3 is a schematic diagram illustrating another embodiment of the fuel supply regulating apparatus of the present invention.

FIG. 3 illustrates a further modification of the fuel supply regulating apparatus of the present invention, in which the housing 21 has connected thereto a fuel inlet nipple 44 through which the fuel 3 enters into the fuel chamber 21a and a fuel outlet nipple 45 through which the fuel 3 is fed to the engine (not shown). Disposed between the outlet nipple 45 and the fuel chamber 21a is a pressure regulating device connected through the rope 30 to the gear 29 driven by the pinion 28a of the motor 28 for regulating the pressure of the fuel 3 in response to the rotation of the gear 29.

Also, it is to be noted that the actuator unit 47 of this embodiment is composed of the differential amplifier 27, the motor 28, the gear 29 and the rope 30, and that the pressure regulating unit 46 is operated directly by the rope 30 connected to the motor 28, and not through the potentiometer 31. The potentiometer 31 of this embodiment may be used for indicating the monitored fuel character or for controlling other actuators.

With this embodiment, the supply pressure of the fuel 3 is regulated by actuating the pressure regulating unit 45 in response to the rotation of the motor 28 which rotates in accordance with the change in characteristics of the fuel 3, so that the fuel combustion conditions can be always maintained at its optimum. Also, the detection of fuel characteristics and the operation of the pressure regulating unit 45 are achieved simultaneously by the common actuator unit 47, the advantages similar to those of the previous embodiments can be obtained. Further, since the pressure regulating unit 45 is actuated without using the potentiometer 31, the overall fuel regulating system can be simplified.

Figure 4:
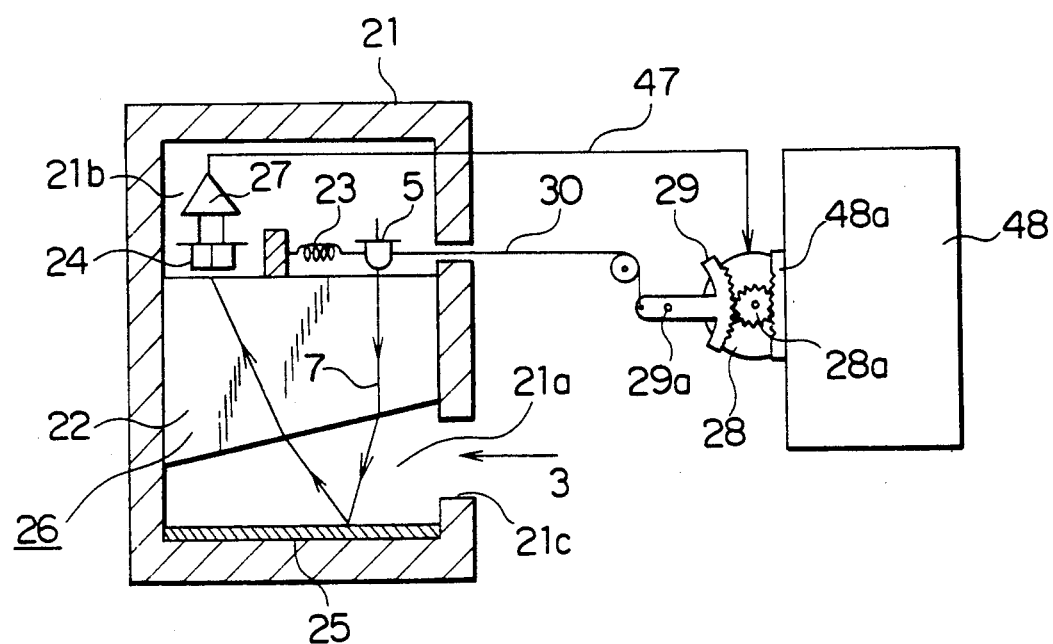
FIG. 4 is a schematic diagram illustrating a further embodiment of the fuel supply regulating apparatus of the present invention.

FIG. 4 illustrates, in a schematic diagram, another embodiment of the fuel supply regulating apparatus of the present invention. In FIG. 4, disposed in the vicinity of the housing 21 is an regulating unit which is a fuel injection timer 48 of a diesel engine. The fuel injection timer 48 has provided with an operating rack 48a slidable for regulating gain of the timer 48.

It is seen that the motor 28 is disposed outside of the housing 21 and the pinion 28a is in engagement with the operating rack 48a. The pinion 28a is also engaged by the gear 29 which is connected to the light source 5 within the housing 21 through the rope 30. The actuator unit 47 of this embodiment is similar to that of the previous embodiment illustrated in FIG. 3 and the other components are similar to those illustrated in FIG. 1.

The output power of the diesel engine is determined by the amount of the fuel 3 injected in the cylinder after air is suctioned. While the usual fuel 3 of a diesel engine is light oil, a mixture of the light oil and an alcohlic fuel is sometimes used. In such case, the output power of the engine is small if the same amount of the fuel 3 as in the case where the fuel 3 contains no alcoholic fuel is injected. Therefore, the fuel supply amount must be changed according to the mixture ratio of the alcoholic fuel is the same output power is to be maintained.

In the above embodiment, when the refraction factor of the fuel 3 is changed, the motor 28 is rotated in accordance with the change in the refraction factor of the fuel 3, and this rotation of the motor 28 causes direct operation of the operating member 47a to regulate the gain of the fuel injection timer 35. Thus, with this embodiment, advantageous results similar to those of the previous embodiments can be obtained.

While the description has been made in terms of the embodiments in which the actuator unit 32, 43 or 47 causes the light source 5 to be displaced or the reflecting mirror 25 to be tilted, this invention is not limited to them and the reflecting mirror 25 may be translatingly moved or the light receiving unit 24 may be displaced. Also, the arrangements of the light path defining unit 26 and the light receiving unit 24 are not limited to those previously described but many modifications can be applied.

As has been described, according to the fuel supply regulating apparatus of the present invention, the actuator unit causes one of the light source, the light path defining unit and the light receiving unit to be displaced so that the light beam is always received at the constant position on the light receiving unit and, at the same time, the regulating unit is operated in correspondence with an amount of the displacement. Therefore, the fuel regulating unit can be directly operated at the same time as the detection of the nature of the fuel, whereby the overall structure of the fuel supply system of the internal combustion engine can be made simple and inexpensive.

What is claimed is:

1. An apparatus for regulating fuel supply according to fuel mixture ratio, comprising:
   a light source for radiating a light beam through a fuel;

light path defining means for defining a light path for said light beam in accordance with a refraction ratio of said fuel;

light receiving means for receiving said light beam passed through the fuel and supplying an output signal indicative of the position at which the light beam impinges upon said light receiving means; and actuator means connected to said light receiving means for moving at least one of said light source, said light path defining means and said light receiving means by an amount sufficient to keep said light beam impinging at a constant position on said light receiving means, said actuator means being connectable to fuel regulator means for adjusting the fuel supply to an engine in accordance with said amount of movement.

2. A fuel supply regulating apparatus as claimed in claim 1, wherein said actuator means comprises a motor rotatable in response to said signal from said light receiving means, a pinion connected to the motor, a sector gear driven by said pinion and connected to said light source for transmitting movement therebetween, and a spring for biasing said light source to its home position.

3. A fuel supply regulating apparatus as claimed in claim 1, wherein said actuator means comprises a motor rotatable in response to said output signal from said light receiving means, a pinion connected to the motor, a sector gear driven by said pinion, a cam connected to said sector gear and in contact with a reflecting mirror of said light path defining means for moving said reflecting mirror, and a spring for biasing said reflecting mirror to its home position.

4. A fuel supply regulating apparatus as claimed in claim 1, wherein said actuator means comprises a motor rotatable in response to said signal from said light receiving means, a pinion connected to the motor, a sector gear driven by said pinion and connected to said light source for transmitting movement of said sector gear to said light source, and a spring for biasing said light source to its home position, said sector gear being also connected to a fuel pressure regulator for regulating the fuel pressure in response to said output signal from said light receiving means.

5. A fuel supply regulating apparatus as claimed in claim 1, wherein said fuel regulator means is a fuel injection timing regulator.

6. A fuel supply regulating apparatus as claimed in claim 1, wherein said actuator means is disposed within said housing.

7. A fuel supply regulating apparatus as claimed in claim 1, wherein said actuator means is disposed outside of said housing.

* * * * *